US010086335B2

(12) United States Patent
Liu et al.

(10) Patent No.: US 10,086,335 B2
(45) Date of Patent: Oct. 2, 2018

(54) COMPOSITION AND METHOD FOR BIOFOULING INHIBITION OF MEMBRANE SEPARATION DEVICE

(71) Applicant: Ecolab USA Inc., St. Paul, MN (US)

(72) Inventors: Yu Tie Liu, Shanghai (CN); Ling Feng Han, Shanghai (CN); Wen Jin Ye, Shanghai (CN); Harshada Lohokare, Kothrud Pune (IN); Wen Li Tu, Shanghai (CN)

(73) Assignee: ECOLAB USA INC., St. Paul, MN (US)

( * ) Notice: Subject to any disclaimer, the term of this patent is extended or adjusted under 35 U.S.C. 154(b) by 64 days.

(21) Appl. No.: 15/032,725

(22) PCT Filed: Oct. 21, 2014

(86) PCT No.: PCT/US2014/061497
§ 371 (c)(1),
(2) Date: Apr. 28, 2016

(87) PCT Pub. No.: WO2015/073170
PCT Pub. Date: May 21, 2015

(65) Prior Publication Data
US 2016/0271565 A1 Sep. 22, 2016

(30) Foreign Application Priority Data
Nov. 12, 2013 (CN) .......................... 2013 1 0560526

(51) Int. Cl.
*B01D 65/08* (2006.01)
*B01D 61/04* (2006.01)
(Continued)

(52) U.S. Cl.
CPC ............. *B01D 65/08* (2013.01); *A01N 59/00* (2013.01); *B01D 61/025* (2013.01);
(Continued)

(58) Field of Classification Search
None
See application file for complete search history.

(56) References Cited

U.S. PATENT DOCUMENTS

2002/0027111 A1 3/2002 Ando et al.
2002/0153329 A1 10/2002 Hempel et al.
(Continued)

FOREIGN PATENT DOCUMENTS

| CN | 102821610 A | 12/2012 |
| CN | 103061206 A | 4/2013 |
| WO | WO 2013/059019 A1 | 4/2013 |

OTHER PUBLICATIONS

International Search Report and Written Opinion for related International Application No. PCT/US2014/061497, dated Jan. 29, 2015 (12 pages).
(Continued)

*Primary Examiner* — Chester T Barry
(74) *Attorney, Agent, or Firm* — Eric D. Babych; Brinks Gilson & Lione

(57) ABSTRACT

This disclosure relates to a combination for inhibiting or removing biofouling and a method for inhibiting biofouling growth or removing biofouling. This disclosure also relates to a combination including halogen-type oxidizers, sulfur-containing compounds, and ammonium salts and/or urea. Also disclosed are methods for inhibiting the biofouling growth in a reverse osmosis membrane separation device or nanofiltration membrane separation device or removing the biofouling in a reverse osmosis membrane separation device or nanofiltration membrane separation device.

17 Claims, 8 Drawing Sheets

(51) Int. Cl.
- *B01D 61/02* (2006.01)
- *B01D 61/10* (2006.01)
- *B01D 65/02* (2006.01)
- *C02F 1/68* (2006.01)
- *A01N 59/00* (2006.01)
- *C02F 1/44* (2006.01)
- *C02F 1/76* (2006.01)

(52) U.S. Cl.
CPC ........... *B01D 61/027* (2013.01); *B01D 61/04* (2013.01); *B01D 61/10* (2013.01); *B01D 65/02* (2013.01); *C02F 1/44* (2013.01); *C02F 1/68* (2013.01); *C02F 1/76* (2013.01); *B01D 2311/04* (2013.01); *B01D 2311/12* (2013.01); *B01D 2321/16* (2013.01); *B01D 2321/162* (2013.01); *B01D 2321/168* (2013.01); *C02F 1/441* (2013.01); *C02F 1/442* (2013.01); *C02F 2303/20* (2013.01)

(56) References Cited

U.S. PATENT DOCUMENTS

| | | |
|---|---|---|
| 2002/0189647 A1 | 12/2002 | Labib et al. |
| 2003/0029812 A1 | 2/2003 | Burns et al. |
| 2003/0064089 A1 | 4/2003 | Kumar |
| 2003/0203827 A1 | 10/2003 | Cooper et al. |
| 2005/0147528 A1 | 7/2005 | Shim et al. |
| 2006/0089285 A1 | 4/2006 | Ahmed et al. |
| 2007/0056904 A1 | 3/2007 | Hogt et al. |
| 2007/0210002 A1 | 9/2007 | Mullette et al. |
| 2008/0169006 A1 | 7/2008 | Musale et al. |
| 2009/0043123 A1 | 2/2009 | Copenhafer et al. |
| 2010/0092574 A1 | 4/2010 | Sweeny |
| 2013/0026097 A1 | 1/2013 | Hirao et al. |
| 2013/0101683 A1 | 4/2013 | Tu et al. |

OTHER PUBLICATIONS

International Search Report and Written Opinion for International Application No. PCT/US2015/054622, dated Jan. 20, 2016 (10 pages).

COMPOSITION AND METHOD FOR BIOFOULING INHIBITION OF MEMBRANE SEPARATION DEVICE

TECHNICAL FIELD

This invention relates to a method for inhibiting the biofouling growth and removing the biofouling in a membrane separation device, such as reverse osmosis membrane separation device or nanofiltration membrane separation device, and relates to a combination for inhibiting the biofouling growth in a membrane separation device or removing the biofouling in a membrane separation device.

BACKGROUND OF THE INVENTION

Biofouling which is formed from the microbes growing on surface of a membrane separation device, especially the biofouling on surface of a reverse osmosis membrane or nanofiltration membrane separation device will add significant negative affect on the osmotic pressure of the membrane separation device such as reverse osmosis membrane (RO membrane). Biofouling also reduces the flow rate and quality of the water produced by the membrane separation device, and increases the operation pressure and pressure drop of the system, and affects the operation of the membrane separation device significantly. During the operation of the membrane separation device, the chemicals which are applied to wash the membrane separation device are usually needed. However, such operation may reduce the service life of the membrane.

Biofouling is a sticky substance that adheres to surface of the objects, which is formed from that the microbes and viscous liquid produced by thereof are mixed with the other organic and inorganic substance. The membrane separation device is usually used to treat water. Organic impurities, inorganic impurities and microbes exist in the water system, and therefore it is easy for biofouling to form on the surface of a membrane separation device. In order to prevent the biofouling adversely affects the membrane separation device, the application of biocides is needed to inhibit the growth of the microbes so as to prevent the generation of biofouling.

Up to now, several non-oxidizing biocides such as DBNPA and isothiazolone have been applied to inhibit the biofouling in RO membrane device. These non-oxidizing biocides can control the growth of the biofouling to a certain level without destroying the membrane material itself of the membrane separation device. However these non-oxidizing biocides are too expensive and normally used in intermittent dosage, and sometimes can not guarantee the sufficient biocidal effect.

Due to the structure of the formed biofouling or biofilm is very dense, and it is typical the composite of the bacteria and extracellular matrix. Therefore, biofouling provides some protection to the organism therein. Usually the dosage of biocides used to kill the microbes in biofouling is 10 to 1000 times higher than that used to kill the same microbes which are obtained by normal cultivation. Additionally, if the growth of biofouling can not be inhibited thoroughly or the biofouling grown can not be removed clearly, the biofouling of microbes which is only killed to a certain level will further provide nutrient for the growing of microbes and promote the growth of microbes reversely. Based on the above, the cost of using non-oxidizing biocides is high, and the killing effect is insufficient, meanwhile it is hard to ensure an effective control on biofouling. Thus, there is a need for developing more effective and lower cost biocides to control the biofouling in the membrane separation device.

Chlorine is a very cheap biocide, and is the most frequently used as biocide, especially for water treatment process. A large amount of chlorine in water may exist in the form of free chlorine. Such free chlorine will oxidize the surface of membrane and reduce the separation ability of membrane, for example, destroy amide bonds of polyamide of RO membrane. Thus, in the water treatment system that typically consists of RO membrane, the chlorine is mainly applied for pretreatment. A dechlorination process within the water environment prior to RO membrane filtration must be performed using reducing agent such as sodium bisulfite. It is impossible to apply the effective chlorine-type biocide to the membrane separation device directly.

Recently, researchers have attempted to use different modified methods to control the biofouling of reverse osmosis membrane separation device or nanofiltration membrane separation device. For example, Louie et al. provided a membrane surface modification technique (J. S. Louie, I. Pinnau, I. Ciobanu, K. P. Ishida, A. Ng, M. Reinhard, Effects of polyether-polyamide block copolymer coating on performance and fouling of reverse osmosis membranes, J. Membr. Sci. 280 (2006) 762-770). The method of applying enzyme was developed by Richards et al. (M. Richards, T. E. Cloete, Nanoenzymes for biofilm removal, In: in: T. E. Cloete, M. Dekwaadsteniet, M. Botes, J. M. Lopez-Romero (Eds.), Nanotechnology in Water Treatment Applications, Caister Academic press, Norfolk, U K, 2010, pp. 89-102). Hilal et al. used filtration process to reduce the concentration of microbes (N. Hilal, H. Al-Zoubi, N. A. Darwish, A. W. Mohamma, M. Abu Arabi, A comprehensive review of nanofiltration membranes: treatment, pretreatment, modeling, and atomic force microscopy, Desalination 170 (2004) 281-308.). Wolf et al. disclosed that remove the nutrient in the feed stream of RO system through filtration process (P. H. Wolf, S. Siverns, S. Monti, UF membranes for RO desalination pretreatment, Desalination 182 (2005) 293-300.). Furthermore, the technique of using UV light (T. Harif, H. Elifantz, E. Margalit, M. Herzberg, T. Lichi, D. Minz, The effect of UV pre-treatment on biofouling of BWRO membranes: a field study, Desalin. Water Treat. 31 (2011) 151-163.), the technique of using electricity (M. I. Kerwick, S. M. Reddy, A. H. L. Chamberlain, D. M. Holt, Electrochemical disinfection, an environmentally acceptable method of drinking water disinfection Electrochim. Acta 50 (2005) 5270-5277) and the technique of using ultrasonic wave (R. A. Al-Juboori, T. Yusaf, V. Aravinthan, Investigating the efficiency of thermosonication for controlling biofouling in batch membrane systems, Desalination 286 (2012) 349-357.) were disclosed respectively. These techniques are still associated with some shortcomings, for example, high cost, insufficient activity on inhibiting biofouling, low stability and applicability. Thus, there is still a need for developing an effective biological inhibitor and a method for controlling biofouling.

The method of controlling biofouling with chemicals is still the most concerned researching directions. The research which used chloramine as biocide was attractive. However when transition metal ions such as Fe ions exist, chloramine still damages RO membrane. Moreover, chloramine is highly influenced by pH during practical operation. When pH reduces to less than 6, chlorine may be produced and it may lead to a potential safety hazard.

Sulfamic acid is a common cleaning agent and also considered as an environment friendly biocide. Sulfamic acid and sulfamate can be used to stabilize halogens and form sulfamic acid halogen products that have a function of preventing bacteria from adhesion to metal or plastic surfaces (U.S. Pat. No. 6,380,182B1 (2002), Thomas E. McNeel, Marilyn S. Whittemore, Stephen D. Bryant, Graciela H. Vunk, Methods and Compositions Controlling Biofouling Using Sulfamic Acids.).

It is noticed that chlorine stabilized by using sulfamic acid can effectively reduce the level of free chlorine in environment without sacrificing total active chlorine. Therefore, the risk of membrane damaged by free chlorine can be minimized as much as possible and an opportunity that utilizes cheaper chlorine as biocides to treat membrane separation device may be provided. Additionally, sulfamic acid-based substances themselves are low cost products and suitable for application in large amounts. Kurita Company has used sulfamic acid to stabilize chlorine and used it as an inhibitor for biofouling of RO membrane (JP 2006-263510). However, the chlorine stabilized by sulfamic acid fails to provide sufficient activity on controlling the growth of biofouling, and there is a limitation on the concentration of application. If the concentration is higher than a certain level, the membrane may be damaged. In order to prevent the membrane from damaging, adding additional reducing agents to RO membrane unit is necessary. For example, adding reducing agents to the concentrated water of the first stage RO so as to neutralize the concentrated stabilized chlorine (JP 2010-201313), which increases the complexity of the operation and is hard to control. Thus, it is desired to find a proper method for inhibiting the growth of biofouling in membrane separation device, especially in reverse osmosis membrane separation device or nanofiltration membrane separation device.

SUMMARY OF THE INVENTION

The present invention is directed toward a method for inhibiting the biofouling growth in a membrane separation device or removing the biofouling in a membrane separation device. Specifically, the present invention is directed to the following aspects.

A method for inhibiting the biofouling growth in a membrane separation device for water treatment or removing the biofouling in a membrane separation device for water treatment is disclosed. The method includes adding halogen-type oxidizers and sulfur-containing compounds or adding the mixture of the halogen-type oxidizers and sulfur-containing compounds to the membrane separation device, followed by adding ammonium salts and/or urea to the membrane separation device. The invention may further include that the sulfur-containing compounds are 1 to 5 moles and the ammonium salts and/or urea are 0.1 to 1.0 moles with respect to 1 mole of the halogen-type oxidizers.

In an embodiment the halogen-type oxidizers are chlorine and bromine-type oxidizers. In a further embodiment the chlorine and bromine-type oxidizers are selected from the group consisting of chlorine, chlorine dioxide, hypochlorous acid and the salts thereof, chlorous acid and the salts thereof, chloric acid and the salts thereof, perchloric acid and the salts thereof, chlorinated isocyanuric acid and the salts thereof, hypobromous acid and the salts thereof, bromous acid and the salts thereof, bromic acid and the salts thereof, perbromic acid and the salts thereof, brominated isocyanuric acid and the salts thereof, and combinations thereof.

In the method of the invention the sulfur-containing compounds may be sulfamic acids represented by the general formula (1) and the salts thereof

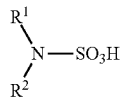

general formula (1)

wherein $R^1$ and $R^2$ each independently represents hydrogen or hydrocarbon groups having 1 to 8 carbon atoms.

In an embodiment of the method of the invention the pH of the mixture of the halogen-type oxidizers and sulfur-containing compounds is 7 or more than 7. In another embodiment the ammonium salts comprise inorganic ammonium salts, such as ammonium sulfate, ammonium chloride, ammonium hydroxide or ammonium phosphate, and organic ammonium such as ammonium acetate, ammonium formate or ammonium propionate. The method further includes the amount of active halogens in the inlet water of the membrane separation device is 0.1 to 100 ppm, or 0.5 to 50 ppm.

The membrane separation device of the method of the invention may be a reverse osmosis membrane separation device or nanofiltration membrane separation device.

The method includes adding sodium hypochlorite and sulfamic acid or adding the mixture of the sodium hypochlorite and sulfamic acid to the membrane separation device, followed by adding ammonium sulfate to the membrane separation device.

The method further includes the sulfamic acid are 1 to 5 moles and the ammonium sulfate are 0.1 to 1.0 moles with respect to 1 mole of the sodium hypochlorite.

The method further includes the amount of active halogens in the inlet water of the membrane separation device is 0.1 to 100 ppm, or 0.5 to 50 ppm.

Another object of the present application is to provide a combination for inhibiting or removing the biofouling, which is used to effectively control the growth of biofouling in a membrane separation device or removing the grown biofouling. Specifically, the present invention is directed toward the following aspects.

A combination for inhibiting or removing the biofouling in a membrane separation device for water treatment is disclosed. The combination includes a first component which is the mixture of halogen-type oxidizers and sulfur-containing compounds, and a second component which is ammonium salts and/or urea, wherein with respect to 1 mole of the halogen-type oxidizers, the sulfur-containing compounds are 1 to 5 moles and the ammonium salts and/or urea are 0.1 to 1.0 moles. In an embodiment the pH of the first component is 7 or more than 7. In another embodiment the halogen-type oxidizers are chlorine and bromine-type oxidizers.

In a further embodiment of the combination of the invention the chlorine and bromine-type oxidizers are selected from the group consisting of chlorine, chlorine dioxide, hypochlorous acid and the salts thereof, chlorous acid and the salts thereof, chloric acid and the salts thereof, perchloric acid and the salts thereof, chlorinated isocyanuric acid and the salts thereof, hypobromous acid and the salts thereof, bromous acid and the salts thereof, bromic acid and the salts thereof, perbromic acid and the salts thereof, brominated isocyanuric acid and the salts thereof, and combinations thereof.

In yet another embodiment the combination of the invention may be practiced wherein the sulfur-containing compounds are sulfamic acids represented by the general formula (1) and the salts thereof.

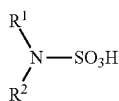

general formula (1)

wherein $R^1$ and $R^2$ each independently represents hydrogen or hydrocarbon groups having 1 to 8 carbon atoms. In a further embodiment of the combination the ammonium salts comprise inorganic ammonium salts, such as ammonium sulfate, ammonium chloride, ammonium hydroxide or ammonium phosphate, and organic ammonium such as ammonium acetate, ammonium formate or ammonium propionate.

The combination includes a first component which is the mixture of sodium hypochlorite and sulfamic acid, and a second component which is ammonium sulfate, wherein with respect to 1 mole of the sodium hypochlorite, the sulfamic acid are 1 to 5 moles and the ammonium sulfate are 0.1 to 1.0 moles.

The present invention relates to applying the combination according to the present invention to inhibit the biofouling growth in a membrane separation device or remove the biofouling in a membrane separation device. The invention further anticipates the use of the combination for inhibiting the biofouling growth in a membrane separation device for water treatment or removing the biofouling in a membrane separation device for water treatment, the use including adding the first component and followed by adding the second component to the membrane separation device; or adding the first component and the second component to the membrane separation device, simultaneously. When using the combination of the invention the amount of active halogens in the inlet water of the membrane separation device is 0.1 to 100 ppm, or 0.5 to 50 ppm.

The membrane separation device may be reverse osmosis membrane separation device or nanofiltration membrane separation device.

Utilizing the method according to the present invention can effectively inhibit the growth of biofouling without damaging the filtration membrane itself which is comprised of polymers (such as polyamide).

The other objects of the present invention will be apparent from the description of the present invention in the present specification. Furthermore, the other features and advantages of the present invention will be described in details in the following description.

DETAILED DESCRIPTION OF THE INVENTION

Figure 1:
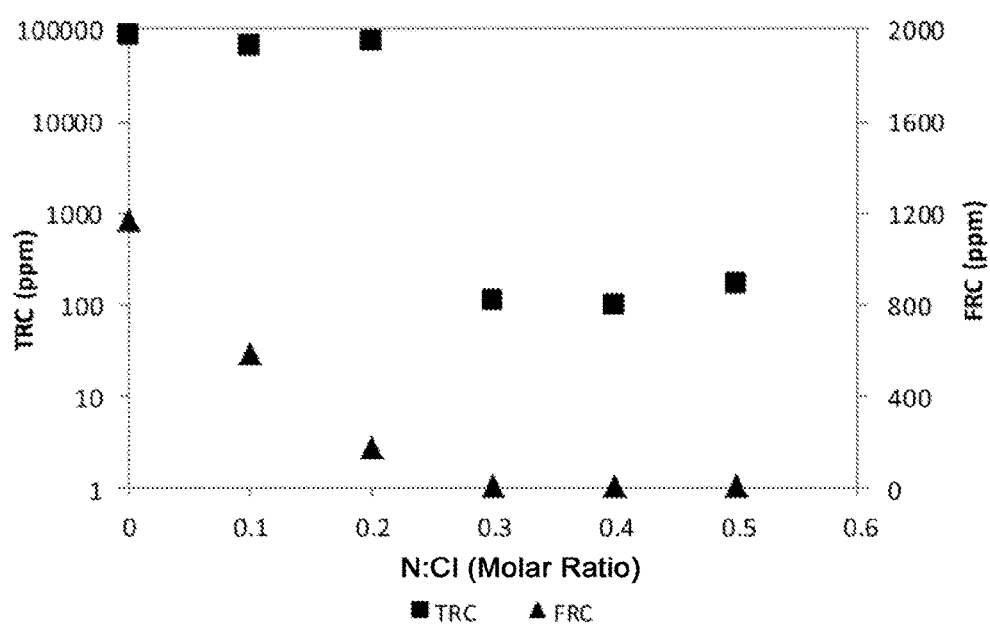
FIG. 1 is a graph that illustrates the effects on concentrations of total chlorine and free chlorine of concentrated solution by changing contents of ammonium sulfate.

The detailed description and the embodiments of the invention will be described in the following.

It should be understood that the meaning of the term used in the present application is the same as the common meaning for those skilled in the art unless it is specifically described. If there is a conflict, the meaning should be understood according to the definition in the present specification. The amounts in the present application mean parts by weight or percent by weight unless they are specifically defined.

The membrane separation device according to the present invention mainly refers to reverse osmosis membrane (RO) and nanofiltration membrane (NF), but also refers to other membrane process such as the membrane separation devices of ultrafiltration membrane (UF), microfiltration membrane (MF) and electrodialysis (ED) and so on. The form of the filtration membrane is not limited, and any type of membrane module such as spiral wound type membrane module, hollow-fiber membrane module, tubular type membrane module, and plane type membrane module and so on can be exemplified. Such membrane separation device can be used to the field of water treatment and can be used for preparation of water such as drinking water, pure water, ultra-pure grade water, the process water for electricity, electronic and semiconductor, the process water for medical field, the water for agents, the water for injection, aseptic pyrogen-free pure water, process water of food and beverage, chemical engineering and other engineering process water, water for boiler, and water for washing and cooling. Such membrane separation device can also be applied to the fields such as desalination of seawater or brackish water.

As the material which forms the membrane, the polymers membrane including nitrogen-containing groups such as aromatic polyamide, polyurea, polypiperazine-amide, etc. can be listed.

In the above water treatment field, the polluting substance, solubilized substance and ionic substance existing in the water to be treated can usually be separated by using the above various kinds of membrane separation devices. However, the microbes in the water to be treated will deposit on the piping line and on the surface of filtration membrane in the whole membrane separation device, and therefore form the biofilm and biofouling, which may influence the osmotic pressures between two sides of the filtration membrane, and finally lead to adversely affect on the water yield passing through the filtration membrane, block the membrane and deteriorate the efficiency of the treatment for impurities.

Due to the membrane-consisting materials are the polymers membrane including nitrogen-containing groups such as aromatic polyamide, polyurea, polypiperazine-amide, etc., which are low resistant to halogen-type oxidizers (one of biocides), if applying the halogen-type oxidizers (such as sodium hypochlorite) directly, it may destroy the material themselves.

One aspect of the present invention relates to the method for inhibiting the biofouling growth in a membrane separation device for water treatment or removing the biofouling in a membrane separation device for water treatment. By applying the method of the present invention, the growth of biofouling can be effectively inhibited without damaging the filtration membrane itself which is comprised of polymers (such as polyamide).

In at least one embodiment, the method for inhibiting the biofouling growth in a membrane separation device or removing the biofouling in a membrane separation device, the method comprising: adding halogen-type oxidizers and sulfur-containing compounds or adding the mixture of the halogen-type oxidizers and sulfur-containing compounds to the membrane separation device, and followed by adding ammonium salts and/or urea to the membrane separation device.

In the above methods, the sulfur-containing compounds use as the first stabilizer for the halogen-type oxidizers, and ammonium salts and/or urea use as the second stabilizer for the halogen-type oxidizers. Halogen-type oxidizers are usually the fluorine-based, chlorine-based and bromine-based oxidizers. The chlorine-based oxidizers or bromine-based oxidizers are frequently used as halogen-type oxidizers.

In at least one embodiment, the chlorine and bromine-type oxidizers are selected from the group consisting of: chlorine, chlorine dioxide, hypochlorous acid and the salts thereof, chlorous acid and the salts thereof, chloric acid and the salts thereof, perchloric acid and the salts thereof, chlorinated isocyanuric acid and the salts thereof, hypobromous acid and the salts thereof, bromous acid and the salts thereof, bromic acid and the salts thereof, perbromic acid and the salts thereof, brominated isocyanuric acid and the salts thereof, and combination thereof. As salts, the alkali metal salts of hypochlorous acid and hypobromous acid such as sodium hypochlorite, sodium hypobromite, potassium hypochlorite and potassium hypobromite; the alkaline earth metal salts of hypochlorous acid and hypobromous acid such as calcium hypochlorite, calcium hypobromite, barium hypochlorite and barium hypobromite; the alkali metal salts of chlorous acid and bromous acid such as sodium chlorite, sodium bromite, potassium chlorite and potassium bromite; the alkaline earth metal salts of chlorous acid and bromous acid such as calcium chlorite, calcium bromite, barium chlorite and barium bromite; other metal salts of chlorous acid and bromous acid such as nickel chlorite; ammonium chlorate and ammonium bromate; the alkali metal salts of chloric acid and bromic acid such as sodium chlorate, sodium bromate, potassium chlorate and potassium bromate; the alkaline earth metal salts of chloric acid and bromic acid such as calcium chlorate, calcium bromate, barium chlorate and barium bromate can be listed. One of these chlorine and bromine-type oxidizers can be used alone or two or more of these chlorine and bromine-type oxidizers can be combined to use. Of the above substances, hypochlorite and hypobromite, especially sodium hypochlorite may be selected due to ease of obtaining.

In at least one embodiment, the first stabilizer of the present invention i.e., the sulfur-containing compounds are sulfamic acid and the salts thereof, which are sulfamic acids represented by the general formula (1) and the salts thereof.

General formula (1)

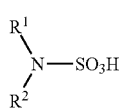

wherein $R^1$ and $R^2$ each independently represents hydrogen or hydrocarbon groups having 1 to 8 carbon atoms.

As specific examples of sulfamic acids represented by the above general formula (1), the sulfamic acid wherein $R^1$ and $R^2$ each independently represents hydrogen, N-methyl sulfamic acid, N,N-dimethyl sulfamic acid and N-phenyl sulfamic acid can be listed. As the salts of sulfamic acid of the present invention, alkali metal salts such as sodium salts and potassium salts; alkaline earth metal salts such as calcium salts, strontium salts and barium salts; other metal salts such as manganese salts, copper salts, zinc salts, ferric salts, cobalt salts and nickel salts; ammonium salts and guanidine salts and so on can be listed. Specifically, sodium sulfamate, potassium sulfamate, calcium sulfamate, strontium sulfamate, barium sulfamate, ferric sulfamate and zinc sulfamate and so on can be used. One of sulfamic acid and the salts thereof can be used alone or two or more of sulfamic acid and the salts thereof can be combined to use.

In at least one embodiment, one of the second stabilizer of the present invention i.e., ammonium salts and urea can be chosen, or both of ammonium salts and urea can be used as the second stabilizer simultaneously. The ammonium salts include the inorganic salt, such as ammonium sulfate, ammonium chloride or ammonium bromide, and organic ammonium such as ammonium acetate, ammonium formate or ammonium propionate. As the ammonium salts, the ammonium sulfate, ammonium chloride or ammonium bromide can be listed.

In at least one embodiment, the halogen-type oxidizers used in the method of the present invention is chlorine-type oxidizers, for example, chlorine, sodium hypochlorite, calcium hypochlorite and potassium hypochlorite, the first stabilizer used is sulfamic acid and the second stabilizer used is ammonium sulfate.

In at least one embodiment, the halogen-type oxidizers used in the method of the present invention is chlorine-type oxidizers, for example, chlorine, sodium hypochlorite, calcium hypochlorite and potassium hypochlorite, the first stabilizer used is sulfamic acid and the second stabilizer used is urea.

In at least one embodiment, the halogen-type oxidizers used in the method of the present invention is bromine-type oxidizers, for example, sodium hypobromite, calcium hypobromite and potassium hypobromite, the first stabilizer used is sulfamic acid and the second stabilizer used is ammonium sulfate.

In at least one embodiment, the halogen-type oxidizers used in the method of the present invention is bromine-type oxidizers, for example, sodium hypobromite, calcium hypobromite and potassium hypobromite, the first stabilizer used is sulfamic acid and the second stabilizer used is urea.

In at least one embodiment, with respect to 1 mole of the halogen-type oxidizers, the sulfur-containing compounds added are 1 to 5 moles, preferably 1 to 2.5 moles, the ammonium salts and/or urea added are 0.1 to 1.0 moles, preferable 0.1 to 0.5 moles. The ammonium salts and/or urea are 0.1 to 1.0 moles means that if using the ammonium salts alone, the amount of ammonium salts is 0.1 to 1.0 moles, or if using urea alone, the amount of urea is 0.1 to 1.0 moles, or if using both of ammonium salts and urea, the total amount of ammonium salts and urea is 0.1 to 1.0 moles.

In at least one embodiment, when applying the method according to the present invention, usually the halogen-type oxidizers and sulfur-containing compounds are mixed, followed by adding them to the inlet water of membrane separation device, and then the ammonium salts and/or urea were added to the inlet water of membrane separation device.

In at least one embodiment, the halogen-type oxidizers and sulfur-containing compounds can be mixed first, and the mixture obtained therefrom is added to the inlet water of membrane separation device, followed by adding the ammonium salts and/or urea to the inlet water (such as water) of membrane separation device. If before adding to the membrane separation device, the halogen-type oxidizers and sulfur-containing compounds are mixed to obtain the mixture and the mixture will keep for a while before applying, the pH of the mixture which consists of halogen-type oxidizers and sulfur-containing compounds can be adjusted to alkaline, and that may keep the mixture stable. If the mixture is added to the membrane separation device immediately after mixing, the pH adjustment can be ignored.

The pH of the mixture of the halogen-type oxidizers and sulfur-containing compounds can be adjusted to basic by using a common basic substrate, such as sodium hydroxide or potassium hydroxide and so on.

In at least one embodiment, the above three components may be added to the inlet water of membrane separation device successively or simultaneously in the present application.

In at least one embodiment, in order to ensure the effective inhibiting effect on biofouling, the amount of active halogen produced from the halogen-type oxidizers in the membrane separation device is 0.1 ppm-100 ppm. It means that the amount of active halogen in the membrane separation device, for example in the inlet water and/or washing water of the membrane separation device is 0.1 ppm-100 ppm.

In at least one embodiment, when applying the method according to the present invention, it is usually desirable to provide 0.1 ppm to 100 ppm of active halogen in water, preferably 0.5 to 50 ppm. The concentration range of the active halogen means the concentration of the active halogen in the inlet water. After the filtration by the membrane, the inlet water may be condensed. Taking the reverse osmosis membrane or nanofiltration membrane as an example, after passing through the membrane filtration process, the condensing multiple is usually 3 to 5 times, for example, 4 times. Therefore, a part of the membranes, such as the membranes at the end of the membrane separation device (with respect to the direction of water flow) may be exposed to an active halogen concentration which has to be condensed several times compared to the original one in the inlet water. For example, when the active halogen concentration in the inlet water is 10 ppm, after passing through the membrane filtration, the active halogen concentration in the water will be increased to for example 40 ppm.

According to the results of examples in the present application (example 5 and example 6), it is known that by applying two stabilizers, the adding dosage of the halogen in the inlet water can be increased so as to enhance the bacteriostatic effect. This is because that when the active halogen concentration is low, such as at 10 ppm, only adding the first stabilizer (i.e., single stabilizer) obtains the similar results as using dual stabilizers. After condensing, however, the active halogen concentration will be increased to such as 40 to 50 ppm, and parts of the membrane are exposed to quite high concentration of active halogen. According to the results of example 6, at high concentration of active halogen, the method with single stabilizer fails to keep the flux and rejection of the membrane separation device constantly, and therefore it is necessary to reduce the active halogen concentration in the original inlet water when using single stabilizer. Such as reducing to far less than 10 ppm, so as to keep the active halogen in the water which is at the end of the membrane module is about 10 ppm. When applying the method of the present invention, the active halogen amount in the inlet water can be increased while the flux and rejection of the membrane are unaffected throughout the operation of the membrane.

When using the chlorine-type oxidizers, the active halogen concentration (amount) can be determined according to the total chlorine detecting method (DPD method) described in the following descriptions. Therefore, the active halogen concentration is the concentration of the active chlorine (total chlorine concentration). That is to say the total chlorine concentration is 0.1 to 100 ppm, preferably 0.5 to 50 ppm.

When using the bromine-type oxidizers, the total bromine concentration can be determined by the DPD method which is the same method as the method for determining the total chlorine. Therefore, the active halogen concentration is the concentration of the active bromine (total bromine concentration). That is to say the total bromine concentration is 0.1 to 100 ppm, preferably 0.5 to 50 ppm.

When using the chlorine-type oxidizers and the bromine-type oxidizers simultaneously, the total chlorine and bromine concentration can be determined by the following DPD method. Therefore, the active halogen concentration is the sum concentration of the active chlorine and bromine (the total chlorine and bromine concentration). That is to say the total chlorine and bromine concentration is 0.1 to 100 ppm, preferably 0.5 to 50 ppm.

By using the method according to the present invention, the biofouling in the membrane separation device, such as in reverse osmosis membrane or nanofiltration membrane can be inhibited effectively, or the biofouling formed are removed effectively without damaging the membrane separation device. It is ensured that the membrane separation device can maintain good performance during the long-term use. In the present invention, the flux and rejection of the membrane separation device are used to characterize the performance of the membrane.

Flux means the amount of the water which pass through unit square area of the membrane per unit time, and it is usually represented by the unit of liter per square meter per hour ($l/m^2 \cdot hr$) or gallon per square foot per day. The flux represents the filtrating water ability of membrane.

Rejection means the presence of removed total solubilized impurities from the inlet water through membrane separation device, which can be calculated according to the following formula:

$$\text{Rejection (\%)} = (1 - \text{the conductivity of the water produced by membrane (the conductivity of the water passed through the membrane filtration)} / \text{the conductivity of the inlet water}) \times 100 \quad \text{(formula 1)}.$$

Through adding the halogen-type oxidizers and sulfur-containing compounds or adding the mixture of the halogen-type oxidizers and sulfur-containing compounds, and then adding ammonium salts and/or urea to the membrane separation device, the flux of the water produced by the membrane separation device and the rejection of the membrane do not decrease, and the chemical washing (backwashing) frequency on the membrane separation device are reduced. Thus, it indicates that the use of the present method inhibits the growth of biofouling effectively in the membrane separation device.

It is usually considered that after adding halogen-type oxidizers to water, the halogen therein typically exists as free form of halogen and combined form of halogen in the water. In the following description, we take sodium hypochlorite as one example of halogen-type oxidizers to describe. When adding such oxidizers for example sodium hypochlorite into water, the element chlorine exist in the form of free chlorine (sometimes abbreviated as FRC in the following description) and in the form of combined chlorine in water. Typically, the sum of the free chlorine and combined chlorine are known as total chlorine (sometimes abbreviated as TC or TRC in the following description). For example, the free chlorines usually exist as the form of hypochlorous acid or ions of hypochlorite. The combined chlorines usually exist as the form of monochloro amine, dichloro amine, nitrogen trichloride and other derivatives of chlorine.

The total chlorine concentration (amount) can be detected according to the following method. The combined chlorine can oxidize the iodide into iodine. The iodine and free chlorine can react with DPD (N,N-Diethyl-p-phenylenediamine) to form a red substance, and which can be used to represent the concentration of the total chlorine (using the absorbance obtained at 530 nm measurement to represent the concentration of total chlorine). The above free chlorine concentration (amount) may be determined by the following method. The free chlorine which may exist in the form of hypochlorous acid or ions of hypochlorite can react with DPD (N, N-Diethyl-p-phenylenediamine) indicator rapidly to form a pink-colored substance, and the strength of such color can be used to indicate the amount of free chlorine, for example the concentration of free chlorine is determined by the measurements of absorbance on 530 nm. The combined chlorine concentration in water is calculated by subtracting free chlorine concentration from total chlorine concentration (i.e., TRC-FRC). In the present invention, TRC and FRC are measured for example by HACH DR2800 spectrophotometer.

It is considered that the free chlorine in water rapidly destroys the membrane separation device; whereas the action of combined chlorine is mild and which can effectively inhibit the growth of microbes without damaging the membrane separation device. Thus, it is desired that the amount of the combined chlorine in the water can be further increased whereas the free chlorine in the water can be reduced.

After mixing the sulfur-containing compounds (the first stabilizer) with the sodium hypochlorite, the amount of free chlorine can be reduced while the combined chlorine amount can be increased. However, according to the discoveries by the applicants, adding sulfur-containing compounds may reduce the free chlorine efficiently, but when the amount of free chlorine achieves a certain level, even adding more sulfur-containing compounds, the amount of free chlorine can not be further reduced. If adding a few amounts of ammonium salts and/or urea (the second stabilizer) at this time, the amount of free chlorine can be reduced significantly, and chloroamine is produced in trace amount. Since by utilizing the present method, the amount of the combined chlorine is high, and the growth of microbes in the membrane separation device can be efficiently inhibited, and thus the forming of biofouling is prevented. Furthermore by utilizing the present method, the free chlorine is further reduced, and it does not exert negative effects on the membrane separation device itself. By adopting the method according to the present invention, during a long-term operation the formation of biofouling in the membrane separation device can be inhibited significantly, and it maintains the separation performance of membrane at a high level during long term, and therefore extends the service life of membrane highly. By using the second stabilizer, the free chlorine in total chlorine is reduced significantly. Therefore even when the total chlorine concentration is relatively high, the free chlorine part which may destroy the membrane device itself can be reduced efficiently.

The method according to the present invention relates to two stabilizers for halogen-type oxidizers. The first stabilizer is sulfur-containing compounds, and the second stabilizer is ammonium salts and/or urea. If the present method only applies the second stabilizer, for example ammonium sulfate, the second stabilizer forms volatile substance easily, and therefore it is hard to control the molar ratios between components, and moreover the combined chlorine obtained is mainly chloroamine in this case. If using the first stabilizer alone, the disadvantages has already be described as above, i.e., even adding more amount of the first stabilizer, the free chlorine amount can not be further reduced efficiently. By combination several kinds of different stabilizers in the present invention, these stabilizers will play synergistically, and which may further reduce the ratio of free chlorine in total chlorine and increase the ratio of combined chlorine in total chlorine, and therefore improve the inhibiting effect without destroying the membrane separation device.

According to another aspect of the present invention, it is referred to a combination for inhibiting or removing the biofouling in a membrane separation device for water treatment, which comprising: a first component which is the mixture of halogen-type oxidizers and sulfur-containing compounds, and a second component which is ammonium salts and/or urea, wherein with respect to 1 mole of the halogen-type oxidizers, the sulfur-containing compounds are 1 to 5 moles and the ammonium salts and/or urea are 0.1 to 1.0 moles.

In the above combination, the halogen-type oxidizers are chlorine and bromine-type oxidizers. The sulfur-containing compounds use as the first stabilizer for halogen-type oxidizers, and the ammonium salts and/or urea use as the second stabilizer for halogen-type oxidizers. Descriptions regarding to the halogen-type oxidizers, the first stabilizer and the second stabilizer are the same as the above corresponding descriptions in the present application.

The components in the combination according to the present invention are added to the inlet stream (such as water) of the membrane separation device batch-wise, sequentially and simultaneously.

Wherein, if the first component is needed to place for a while before application, the pH of the first component can be adjusted to the area of alkaline, which may maintain the stability of the first component efficiently.

In this case, in order to ensure the efficient biofouling-inhibiting effect, the amount of active halogen produced by halogen-type oxidizers in the membrane separation device is 0.1 ppm to 100 ppm, preferably 0.5 to 50 ppm. It means the amount of the active halogen in the inlet stream of the membrane separation device, such as water is 0.1 ppm to 100 ppm, preferably 0.5 to 50 ppm.

By adding the above combination, when one mole of halogen-type oxidizers is added, 1 to 5 moles of sulfur-containing compounds and 0.1 to 1.0 moles of ammonium salts and/or urea are added accordingly. By adding according to the above ratio and maintaining the active halogen concentration at the range of 0.1 ppm to 100 ppm, preferably 0.5 to 50 ppm, the growth of biofouling in the membrane separation device can be inhibited efficiently, or removing the biofouling formed efficiently. Thus the membrane separation device maintains good membrane performance.

In at least one embodiment, the combination of the present invention includes a first component which is the mixture of sodium hypochlorite and sulfamic acid, and a second component which is ammonium sulfate, wherein with respect to 1 mole of the sodium hypochlorite, the sulfamic acid are 1 to 5 moles and the ammonium sulfate are 0.1 to 1.0 moles. When using the combination of the invention the amount of active chlorine (total chlorine) in the inlet water of the membrane separation device is 0.1 to 100 ppm, or 0.5 to 50 ppm.

When applying the method or the combination of the present invention to the membrane separation device so as to inhibit the growth of biofouling or remove the biofouling, the free chlorine in the water can be reduced and the combined chlorine ratio in the total chlorine can be increased. Thus the biofouling in the membrane separation device is inhibited or the biofouling produced is removed efficiently without destroying the membrane separation device, and ensuring that the membrane separation device keeps the good performance during long-term use.

EXAMPLES

The present invention is further explained by the following examples.

Example 1. Adding the Second Stabilizer to the Concentrated Solution to Further Reduce FRC In order to further reduce the FRC, the second stabilizer ammonium sulfate was used in the present example. The results of example 1 are shown in FIG. 1. In the present example, 67 g sodium hypochlorite and 13 g sulfamic acid (sulfamic acid ≥99.5%, AR, Sinopharm Chemical Reagent Co. Ltd.) were first added to 20 g water. The molar ratio between sulfamic acid and sodium hypochlorite was 1.2 to 1. Then the pH was adjusted to more than 12 by sodium hydroxide. According to the addition amount of sodium hypochlorite, the different molar ratios of second stabilizer ammonium sulfates were added. After the solution was uniformly mixed, DPD and iodine were used to determine the TC concentration and DPD was used to determine the FRC concentration.

It can be seen from the results shown in FIG. 1 that after adding the second stabilizer, the FRC concentration reduced rapidly with the increase of the second stabilizer. When addition amount of the second stabilizer reached 0.3 moles with respect to 1 mole of sodium hypochlorite, the free chlorine reduced from 1200 ppm to about 40 ppm without affecting the total chlorine. It is known that adding a small amount of the second stabilizer, the ratio of the free chlorine in the total chlorine can be reduced significantly. However, with further increasing the amount of the second stabilizer, the total chlorine amount reduced.

Figure 2:
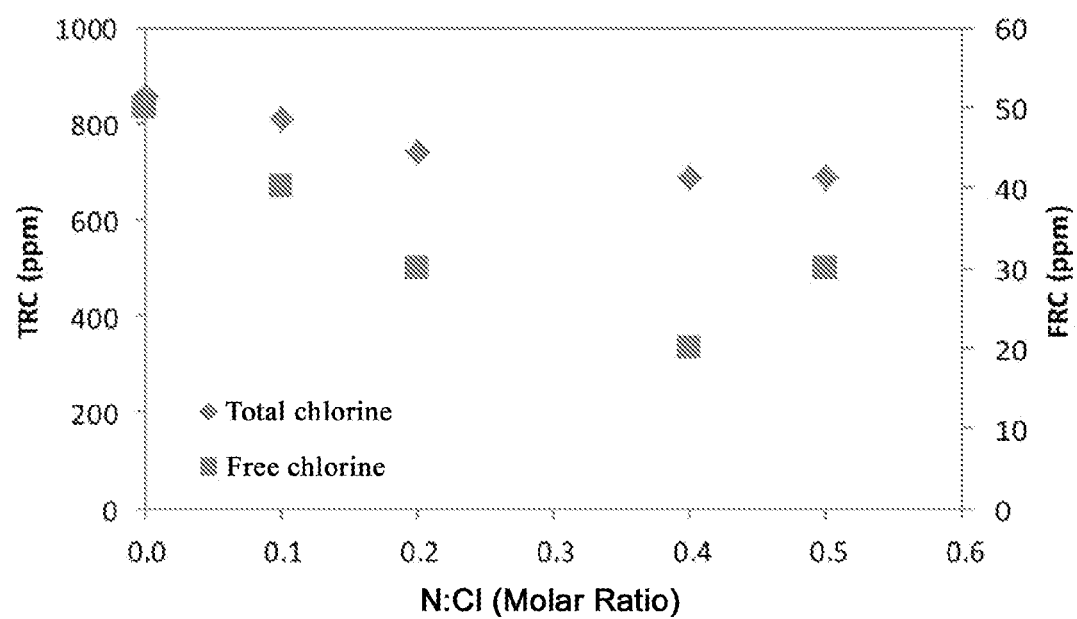
FIG. 2 is a graph that illustrates the effects on concentrations of total chlorine and free chlorine of dilute solution by changing contents of ammonium sulfate.

Example 2. Adding the Second Stabilizer to the Dilute Solution to Further Reduce FRC In the present example, the second stabilizer ammonium sulfate was used in dilute solution to research the reducing effect on FRC. The results of example 2 are shown in FIG. 2. In the present example, 67 g sodium hypochlorite and 13 g sulfamic acid (sulfamic acid ≥99.5%, AR, Sinopharm Chemical Reagent Co. Ltd.) were first added to 3020 g water. The molar ratio between sulfamic acid and sodium hypochlorite was 1.2 to 1. Comparing to the concentration of the sodium hypochlorite and sulfamic acid of the example 1, that of the example 2 was diluted to about 30 times. Then the pH was adjusted to more than 12 by sodium hydroxide. According to the addition amount of sodium hypochlorite, the different molar ratios of second stabilizer ammonium sulfates were added. After the solution was mixed uniformly, DPD and iodine were used to determine the TC concentration and DPD was used to determine the FRC concentration.

It can be seen from the results of FIG. 2 that when addition amount of the second stabilizer reached 0.4 moles with respect to 1 mole of sodium hypochlorite, the FRC concentration reduced rapidly, from about 50 ppm to about 20 ppm without affecting the total chlorine amount. It is known that the second stabilizer amount in the dilute solution can be increased so as to further reduce the free chlorine. Since in actual application, the solution is usually the dilute solution, which looks like the solution of example 2, adding the second stabilizer does not decrease the amount of total chlorine whereas reduce the free chlorine amount significantly.

Example 3. The Bactericidal Effect on the Bacteria in Water

Figure 3:
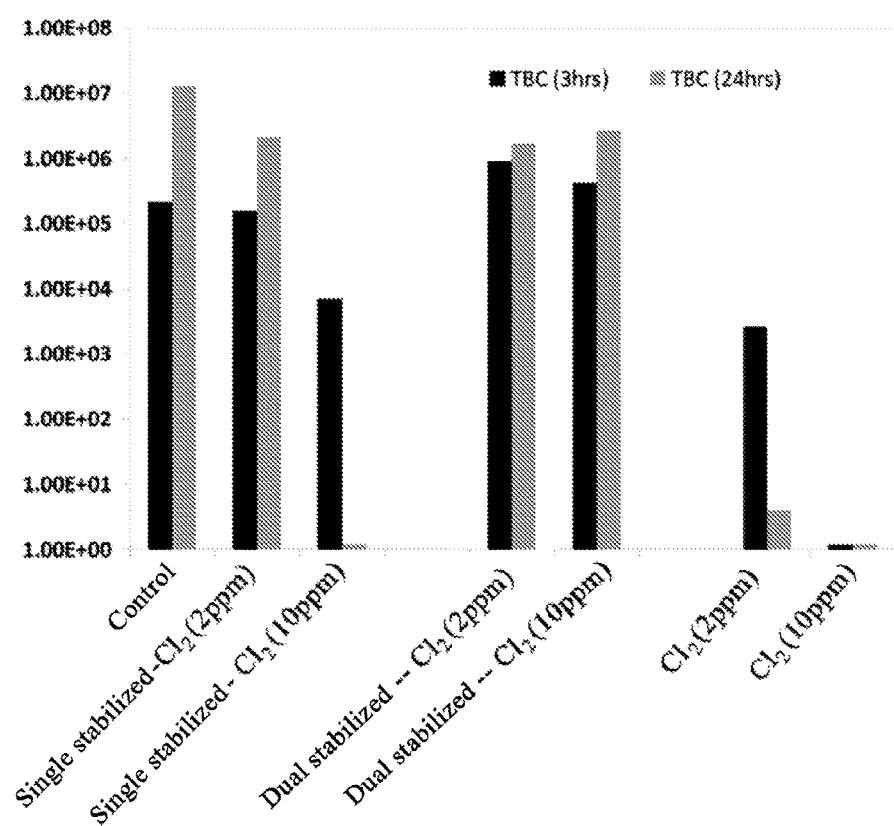
FIG. 3 is a graph that illustrates the biocidal effect of biocides on the bacteria in water.

This example is mainly focused on using the present method or combination to inhibit the floating bacteria in water. The raw water without adding any biocides was used as the control group. The total chlorine concentration in water was controlled at 2 ppm and 10 ppm, separately. Sodium hypochlorite and two kinds of stabilizers were added to the raw water and sample obtained was used as the experimental group (dual stabilizers). Moreover, the group wherein only sodium hypochlorite was added was the control experimental group 1 ($Cl_2$) and the group wherein sodium hypochlorite and one stabilizer were added to the raw water was the control experimental group 2 (single stabilizer). In the control experimental group 1 and 2, the total chlorine concentrations were controlled at 2 ppm and 10 ppm, separately. The addition method of the above substances and the substances used were identical to the examples 1 or 2. The molar ratio between the first stabilizer and sodium hypochlorite was 1.2 to 1. The second stabilizer was added in the amount such that the molar ratio between the second stabilizer and sodium hypochlorite was 0.1 to 1. After placing the control group, the control experimental group 1, 2 and the experimental group for 3 hours and 24 hours, the number of the bacteria in the water of these samples were determined and compared. The results are shown in FIG. 3. The bacterial number was indicated by the Total Bacteria Count (sometimes abbreviated as TBC in the following description), which was determined by referencing the method of 3M™ Petrifilm™ Aerobic Count Plates.

It can be seen from the results shown in FIG. 3 that the sodium hypochlorite has the strongest bactericidal effect. The biocides with adding only the first stabilizer are stronger than the biocides with adding the first stabilizer and the second stabilizer in view of bactericidal effect. It is known that the bactericidal effect becomes mild after adding stabilizers.

Example 4. Inhibiting Effect on the Growth of Biofilm

Figure 4:
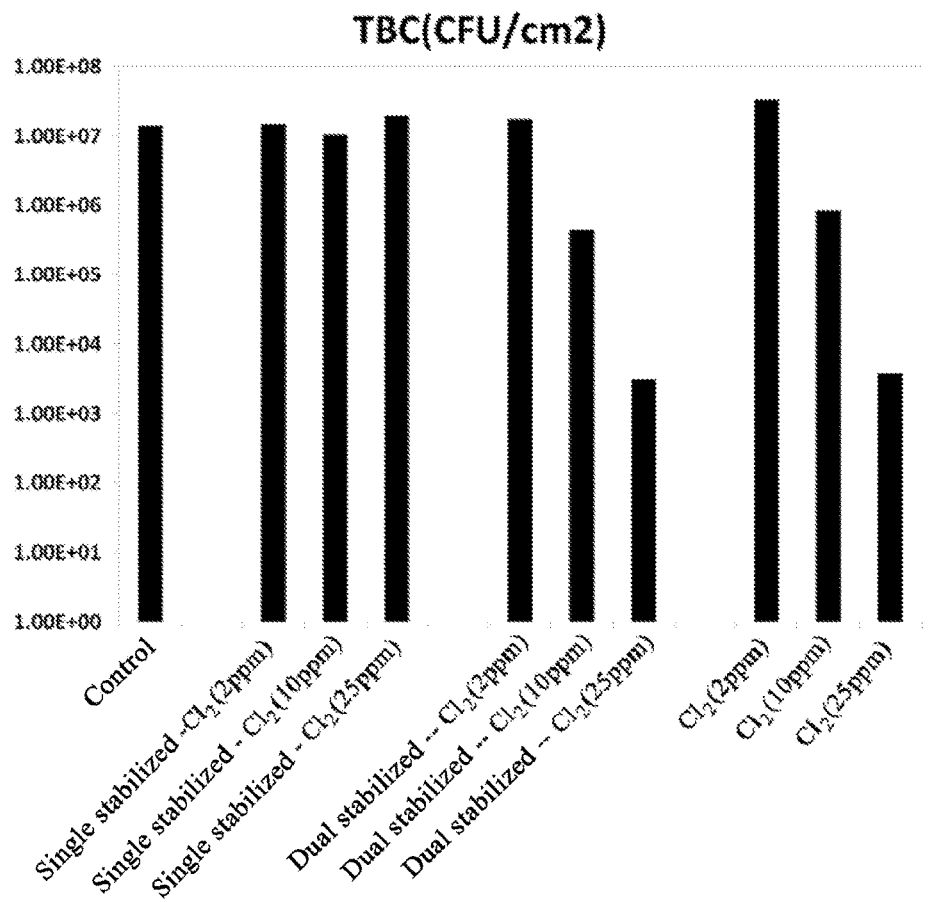
FIG. 4 is a graph that illustrates the inhibition effect of biocides on the growth of biofilm.

This example is mainly focused on the inhibiting effect of the present method or combination on the organism growing on the membrane surface. The raw water without adding any biocides was used as the control group. The total chlorine concentration in the water was controlled at 2 ppm, 10 ppm and 25 ppm, separately. Sodium hypochlorite and two kinds of stabilizers were added to the raw water and the sample obtained was used as the experimental group (dual stabilizers). Moreover, the group wherein only sodium hypochlorite was added was the control experimental group 1 (Cl$_2$) and the group wherein sodium hypochlorite and one stabilizer were added to the raw water was the control experimental group 2 (single stabilizer). In the control experimental group 1 and 2, the total chlorine concentrations were controlled at 2 ppm, 10 ppm and 25 ppm, separately. The addition method of the above substances and the substances used were identical to the examples 1 or 2. The ratio molar between the first stabilizer and sodium hypochlorite was 1.2 to 1. The second stabilizer was added in the amount such that the molar ratio between the second stabilizer and sodium hypochlorite was 0.1 to 1. And then, the cut membrane pieces were put into the prepared water samples as above, and were held at 35° C. for 72 hours. After that, the bacterial numbers on the membrane pieces taken from the water were detected, and the results are shown in FIG. 4. In this example, the bacterial numbers on the membranes were tested by taking the membrane pieces out of the water samples and then dispensing the bacteria on the membrane into the sterile water, and finally determining the bacterial number of the water. Wherein, the bacterial number is indicated by the TBC which is the same as the above description.

According to the results shown in FIG. 4, after running for 3 days, the inhibiting effect on the bacteria growing on membrane surface with adding two stabilizers significantly surpassed that of the biocides with adding only sulfamic acid i.e., one stabilizer (especially when controlling the total chlorine concentrations at 10 ppm and 25 ppm). The bacterial inhibiting effect on the membrane surface with dual stabilizers is equivalent to that of using sodium hypochlorite alone. It is known that using dual stabilizers obtains good bactericidal effect.

Example 5. The Effect on the Membrane Performance by Using the Biofouling Inhibitor with Dual Stabilizers The object of this example is to research the effect on the membrane performance when the membrane is contacting with the biocides during a long time. The 10 ppm and 50 ppm of the biocides (halogen-type oxidizers), in terms of total chlorine in the inlet water were examined to check the effects on the membrane performance. In this example, the continuous operational small plate types reverse osmosis membrane (the model of the reverse osmosis membrane is BW30, produced by Dow Chemical company) separation device was utilized. The available membrane area of the reverse osmosis membrane device for evaluation was 149 square centimeters. The device was operating in the manner of closed circulation and total reflux. The dual stabilizers and biocides (halogen-type oxidizers) were added directly into the raw water box. The addition method of the above substances and the substances used were identical to the examples 1 or 2. The molar ratio between the first stabilizer and sodium hypochlorite was 1.2 to 1. The second stabilizer was added in the amount such that the molar ratio between the second stabilizer and sodium hypochlorite was 0.1 to 1. Applying the standard reverse osmosis membrane testing condition, i.e., the 2000 ppm sodium chloride salts solution was used as raw material solution, the operation pressure was 225 psi and the system was running continuously for 1000 hours. The membrane performance was detected periodically while detecting and maintaining the concentration of biocides in water.

Figure 5A:
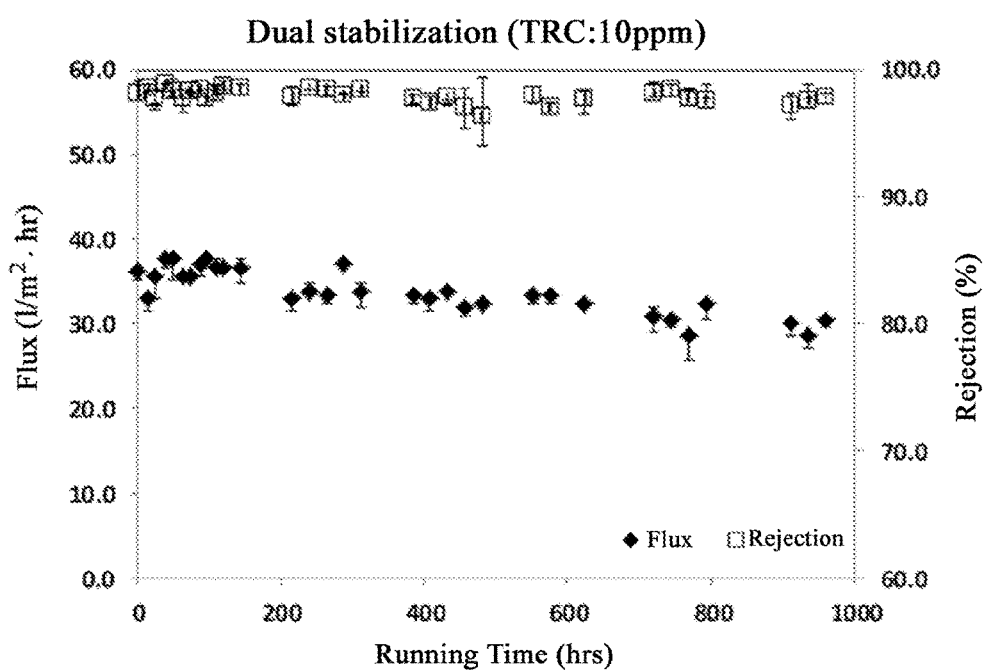
FIG. 5A and FIG. 5B are graphs that illustrate the 1000 hours operation condition in the membrane separation devices when the total chlorine concentrations of the dual stabilizers stabilized biocide are 10 ppm and 50 ppm, respectively.

In this example, during the 1000 hours operation, the volume of the water which passed through the membrane filtration was detected periodically to calculate the flux. Meanwhile, the conductivity of the water produced by membrane and the conductivity of the raw water were detected so as to calculate the rejection (%) according to the above formula 1. The FIG. 5A and FIG. 5B indicate the operation conditions of the membrane separation device during 1000 hours when the total chlorine concentration is 10 ppm and 50 ppm, respectively. It can be seen from the FIG. 5A and FIG. 5B that during 1000 hours operation, the water amount produced by the membrane (flux) and the rejection are kept stable. It is suggested that the method or combination according to the present invention shows good compatibility on reverse osmosis membrane.

Figure 5B:
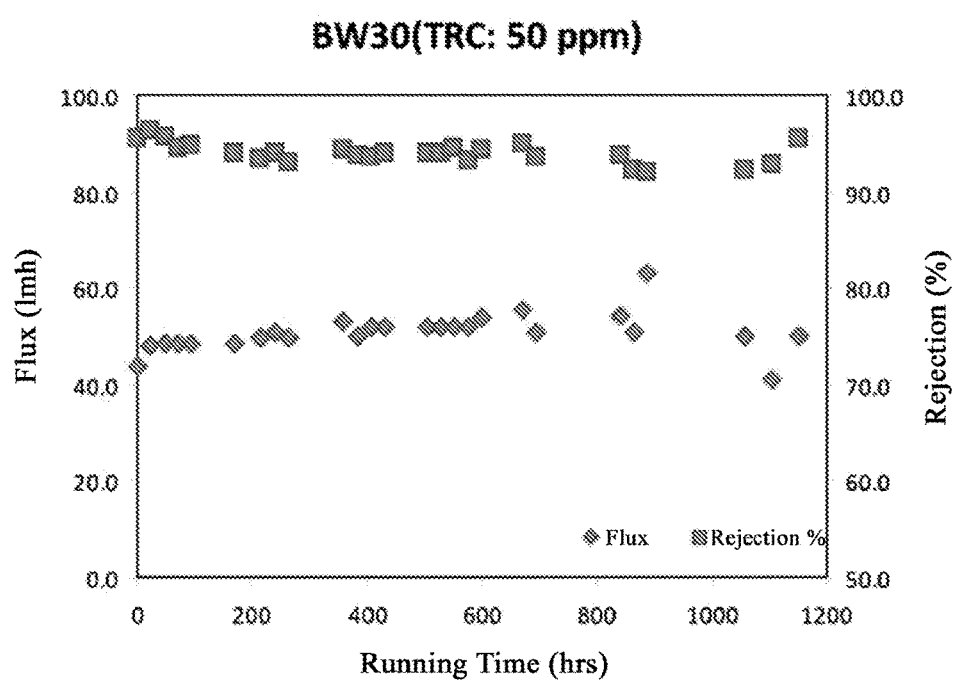
Figure 6A:
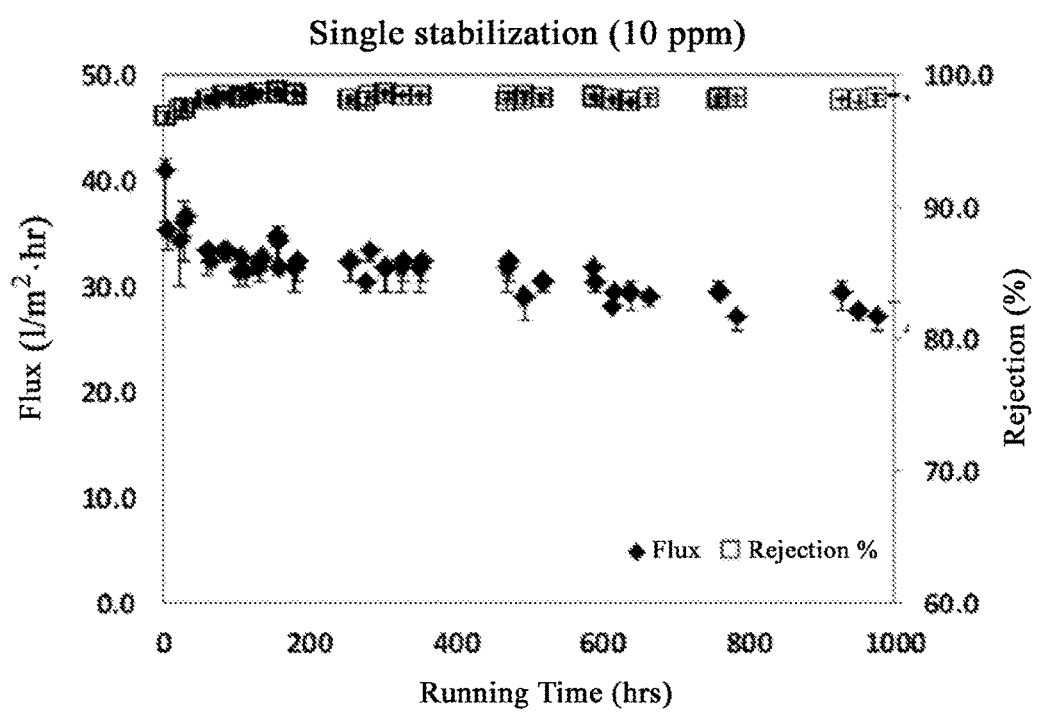
FIG. 6A and FIG. 6B are graphs that illustrate the 1000 hours operation condition in the membrane separation devices when the total chlorine concentrations of the single stabilizer stabilized biocide are 10 ppm and 50 ppm, respectively.
Figure 6B:
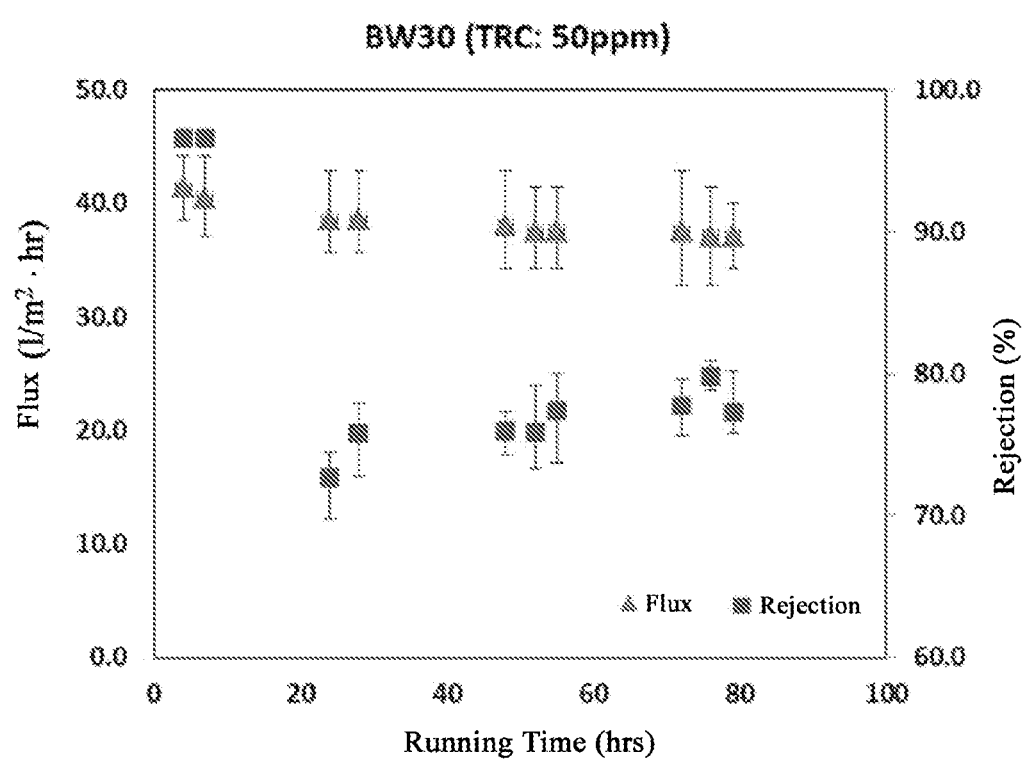

Example 6. The Effect on the Membrane Performance by Using the Biofouling Inhibitor with Single Stabilizer The object of example 6 is to research the effect on the membrane performance when using single stabilizer to form the composition. The specific conducting method and conditions were the same as example 5 except that the biocide composition added to water was obtained from single stabilizer. The molar ratio between sulfamic acid and sodium hypochlorite was 1.2 to 1. The flux and rejection of the membrane were determined by the same methods described in example 5, and the results obtained are listed in FIG. 6A and FIG. 6B. According to the results shown in the figures, when the total chlorine concentration is 10 ppm, the flux and rejection of the membrane with signal stabilizer are both similar to those with dual stabilizers. Both are good. When the total chlorine concentration is 50 ppm, the rejection of the oxidizer with single stabilizer reduces rapidly at the beginning, and reduces from 98% to less than 80% when running for 20 hours (FIG. 6B), which indicates that the stable chlorine obtained by using single stabilizer still leads to damage the membrane and decrease the membrane performance. However, these problems can be avoided by applying dual stabilizers to obtain the stable chlorine (FIG. 5B).

While this invention may be embodied in many different forms described in detail herein are specific embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety for all purposes. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for inhibiting biofouling formation in membrane separation devices for water treatment or removing the biofouling from membrane separation devices for water treatment, the method comprising:
adding halogen-type oxidizers and sulfur-containing compounds or adding a mixture of the halogen-type oxidizers and sulfur-containing compounds to the membrane separation device, and adding ammonium salts and/or urea to the membrane separation device,
wherein the sulfur-containing compounds are sulfamic acids represented by the general formula (1) and the salts thereof,

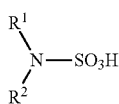

General formula (1)

wherein $R^1$ and $R^2$ each independently represents hydrogen or hydrocarbon groups having 1 to 8 carbon atoms.

2. The method of claim 1, wherein with respect to 1 mole of the halogen-type oxidizers, the sulfur-containing compounds are 1 to 5 moles and the ammonium salts and/or urea are 0.1 to 1.0 moles.

3. The method of claim 1, wherein the halogen-type oxidizers are chlorine and bromine-type oxidizers.

4. The method of claim 3, wherein the chlorine and bromine-type oxidizers are selected from the group consisting of: chlorine, chlorine dioxide, hypochlorous acid and the salts thereof, chlorous acid and the salts thereof, chloric acid and the salts thereof, perchloric acid and the salts thereof, chlorinated isocyanuric acid and the salts thereof, hypobromous acid and the salts thereof, bromous acid and the salts thereof, bromic acid and the salts thereof, perbromic acid and the salts thereof, brominated isocyanuric acid and the salts thereof, and combinations thereof.

5. The method of claim 1, wherein a pH of the mixture of the halogen-type oxidizers and sulfur-containing compounds is 7 or more.

6. The method of claim 1, wherein the ammonium salts comprise inorganic ammonium salts and/or organic ammonium salts.

7. The method of claim 3, wherein the amount of active halogens in the inlet water of the membrane separation device is 0.1 to 100 ppm.

8. The method of claim 1, wherein the membrane separation device is a reverse osmosis membrane separation device or a nanofiltration membrane separation device.

9. A combination for inhibiting or removing biofouling in a membrane separation device for water treatment, the combination comprising:
a first component which is a mixture of halogen-type oxidizers and sulfur-containing compounds, and
a second component which is an ammonium salt and/or urea,
wherein with respect to 1 mole of the halogen-type oxidizers, the sulfur-containing compounds are 1 to 5 moles and the ammonium salts and/or urea are 0.1 to 1.0 moles,
wherein the sulfur-containing compounds are sulfamic acids represented by the general formula (1) and the salts thereof,

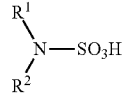

General formula (1)

wherein $R^1$ and $R^2$ each independently represents hydrogen or hydrocarbon groups having 1 to 8 carbon atoms.

10. The combination of claim 9, wherein the halogen-type oxidizers are chlorine and bromine-type oxidizers.

11. The combination of claim 9, wherein the ammonium salts comprise inorganic ammonium salts and/or organic ammonium salts.

12. The combination of claim 9,
wherein the first component is a mixture of sodium hypochlorite and a sulfamic acid represented by the general formula 1, and
the second component is ammonium sulfate,
wherein with respect to 1 mole of the sodium hypochlorite, the sulfamic acid is 1 to 5 moles and the ammonium sulfate is 0.1 to 1.0 moles.

13. A method of using the combination of claim 9, for inhibiting biofouling formation in a membrane separation device for water treatment or removing the biofouling in a membrane separation device for water treatment, the use comprising:
adding the first component and subsequently adding the second component to the membrane separation device; or
adding the first component and the second component to the membrane separation device, simultaneously.

14. The method of claim 13, wherein an amount of active halogens present in water feeding into the membrane separation device is 0.1 to 100 ppm.

15. The method of claim 12, for inhibiting the biofouling growth in a membrane separation device for water treatment or removing the biofouling in a membrane separation device for water treatment, the use comprising:
adding the first component and subsequently adding the second component to the membrane separation device; or
adding the first component and the second component to the membrane separation device, simultaneously.

16. The method of claim 15, wherein an amount of active chlorine present in water feeding into the membrane separation device is 0.1 to 100 ppm.

17. The method of claim 13, wherein the membrane separation device is a reverse osmosis membrane separation device or a nanofiltration membrane separation device.

* * * * *